(12) United States Patent
Ek

(10) Patent No.: US 7,163,541 B2
(45) Date of Patent: Jan. 16, 2007

(54) TIBIAL RESURFACING SYSTEM

(75) Inventor: Steven Ek, Bolton, MA (US)

(73) Assignee: Arthrosurface Incorporated, Stoughton, MA (US)

( * ) Notice: Subject to any disclaimer, the term of this patent is extended or adjusted under 35 U.S.C. 154(b) by 532 days.

(21) Appl. No.: 10/308,718

(22) Filed: Dec. 3, 2002

(65) Prior Publication Data

US 2004/0106928 A1   Jun. 3, 2004

(51) Int. Cl.
*A61B 17/56* (2006.01)

(52) U.S. Cl. ...................................... 606/96

(58) Field of Classification Search ....... 623/20.32–34, 623/20.15, 20.42; 606/73, 95, 96
See application file for complete search history.

(56) References Cited

U.S. PATENT DOCUMENTS

| 5,127,920 | A |   | 7/1992  | MacArthur ................. 623/22 |
| 5,601,550 | A |   | 2/1997  | Esser ........................ 606/54 |
| 5,632,745 | A |   | 5/1997  | Schwartz .................... 606/75 |
| 5,882,350 | A | * | 3/1999  | Ralph et al. ................. 606/61 |
| 6,004,323 | A | * | 12/1999 | Park et al. ................... 606/61 |
| 6,159,216 | A |   | 12/2000 | Burkinshaw et al. ......... 606/88 |
| 6,299,648 | B1| * | 10/2001 | Doubler et al. .......... 623/23.18 |
| 6,342,075 | B1|   | 1/2002  | MacArthur .............. 623/20.14 |
| 6,375,658 | B1|   | 4/2002  | Hangody et al. ............. 606/80 |
| 6,783,550 | B1|   | 8/2004  | MacArthur .............. 623/20.14 |
| 2001/0039455 | A1 | * | 11/2001 | Simon et al. ........... 623/23.51 |
| 2004/0133276 | A1 |   | 7/2004  | Lang et al. .............. 623/14.12 |
| 2005/0015153 | A1 |   | 1/2005  | Goble et al. ............ 623/23.46 |
| 2005/0143731 | A1 |   | 6/2005  | Justin et al. ................. 606/53 |
| 2005/0143745 | A1 |   | 6/2005  | Hodorek et al. .............. 606/87 |
| 2005/0143831 | A1 |   | 6/2005  | Justin et al. ............ 623/20.17 |
| 2006/0004461 | A1 |   | 1/2006  | Justin et al. ............ 623/20.34 |

FOREIGN PATENT DOCUMENTS

WO    WO 02/086180 A2    10/2002

OTHER PUBLICATIONS

"Preliminary Results of Partial Surface Replacement of the Femoral Head in Osteonecrosis", M. Siguier, T. Judet, T. Siguier, G. Charnley, B. Brumpt and I. Yugue, The Journal of Arthroplasty, vol. 14, No. 1, pp. 45-51, 1999.

(Continued)

*Primary Examiner*—Thomas Barrett
*Assistant Examiner*—David A. Izquierdo
(74) *Attorney, Agent, or Firm*—Grossman, Tucker, Perreault & Pfleger, PLLC

(57) ABSTRACT

A tibial resurfacing system is provided that includes a drill guide, bone chisel and implant. In one aspect, the system includes a drill guide that includes a targeting ring and a bore section for creating an axis through the tibia to the superior tibial surface in the vicinity of the targeting ring. In another aspect, a bone chisel is provided that includes a bone-cutting end, having a transverse angle creating an elliptical bone-cutting face. In another aspect, an implant is provided that includes an angled bearing element formed of a cylindrical member having a first end defining a load-bearing surface, and a second end. The first end is formed at an angle that creates an elliptical face of the first end.

13 Claims, 13 Drawing Sheets

OTHER PUBLICATIONS

"Partial Resurfacing Arthroplasty of the Femoral Head in Avascular Necrosis-Methods, Indications, and Results", T. Siguier, M. Siguier, T. Judet, G. Charnley and B. Brumpt, Clinical Orthopaedics and Related Research, No. 386, pp. 85-90, 2001.

EPO Search Report, EPO Application No. 03026286.9, dated Apr. 27, 2004, 6 pgs.

ARTICLE—"Arthroscopically Assisted Treatment of Tibial Plateau Fractures", Suganuma, Jun and Akutsu, Seiji, The Journal of Arthroscopic and Related Surgery, vol. 20, No. 10, Dec. 2004, pp. 1084-1089.

EPO Examination Report dated Feb. 22, 2005, received in corresponding EPO Application No. 01 932 833.5 (3 pgs).

EPO Office Action for European Application No. 03 026 286.9—2310 including remarks, dated Aug. 23, 2004, 4 pgs.

EPO Office Action dated Mar. 15, 2005, received in corresponding EPO Application No. 03 026 286.9 (3 pgs).

* cited by examiner

TIBIAL RESURFACING SYSTEM

FIELD OF THE INVENTION

The present invention relates generally to the field of orthopedic joint replacement, and particularly, to the field of orthopedic joint replacement of the knee.

BACKGROUND OF THE INVENTION

In the field of orthopedic joint replacement of the knee, a relatively recent evolution of the art has resulted in prosthetics that require less removal of bone stock as the preparation for the implantation of the prosthetic devices. This trend in technique and prosthetic design is primarily aimed at creating more options for the orthopedic surgeon when challenged with treating a young active individual with joint disease. It has now become well accepted that treating this individual with a total joint arthroplasty (prosthetic) will be an effective way of relieving the symptoms of pain, but this younger patient will likely place demands on his prosthetic joint that will result in the rapid wear, loosening, and need for replacement of the implants.

In the natural knee, loads transmitted to the joint surfaces during normal activities such as running, walking, and jumping create harsh environments for the articular surface tissues. These articular surface tissues consisting of hyaline cartilage play a key role in the load distribution and impact absorption capability of the knee. The wear and degradation of these tissues is typically the endpoint, which creates symptoms of pain and eventually drives an individual to consider joint replacement surgery.

However, many structures and tissues in the joint as well as the musculature of the leg play a complex role in the distribution and management of the loads ultimately seen by the articular surfaces. Arguably one of the most important of these is the meniscus. The meniscus is a kidney-bean shaped structure which attaches to the top articular surface of the tibia with two bony inserts, one anteriorly and one posteriorly. The meniscus is contoured so that it matches the surface of the tibial articular surface on its underside and matches the convex curve of the mating femoral articular surface on its topside. It is comprised of a highly organized system of fibrous bands that are circumferential and give the structure its hoop strength characteristics. In this capacity, the meniscus is understood to significantly increase the contact surface area of the joint so that loads are more evenly distributed over a greater area of both the femoral and tibial hyaline cartilage surfaces. For this reason, there is great advantage to try to preserve this structure.

In prosthetic knee joints, one of the greatest causes of failure is based on wear debris of the tibial component. Not only does this result in the wear of the tibial component but also produces small wear debris particles which stimulate osteolysis, inflammatory changes in neighboring tissues, and eventual loosening of the implant.

Modern prosthetic joint design relies on a careful contour matching of the tibial component, typically composed of ultra-high molecular weight polyethylene (UHMWPE), to the femoral component, typically composed of a Cobalt-Chrome Alloy (CoCr). Mismatch of the surfaces or misalignment of the surfaces during surgical implantation will cause accelerated wear and early failure of the joint. However, as a function of the complex mechanics of the knee, even in the event of perfect surgical matching and alignment of the two components, there are still articulations of the prosthetic joint that create very concentrated local or even point loads between the two components, which result in the creation of a shear particle from the UHMWPE surface.

There would be a great advantage in developing a tibial component prosthetic component that could be implanted without requiring the removal of the meniscus. This component could effectively resurface only a portion of the overall tibial surface, so that the worn exposed portion of the tibial articular cartilage would be replaced, but areas of the tibial surface underlying the meniscus, and the insertion sites of the meniscus would remain intact. This implant would preserve as much normal knee anatomy and load bearing tissue as possible in an attempt to eliminate concentrated loads or point loads between a femoral component (as appears in previous patents) and the described tibial component. A system of instruments useful in locating, positioning and delivering the prosthetic is included.

SUMMARY OF THE INVENTION

Accordingly, in one aspect the present invention provides a drill guide for positioning a drill along an axis defined through a tibia bone and through a superior tibial surface, the axis is formed at an angle with respect to the long axis of the tibia, and the superior tibial surface bounded at least partially by a meniscus of a knee. The drill guide includes a targeting ring portion having at least one dimension sized to be equal to or less than the superior tibial surface bounded by the meniscus of the knee.

In another aspect, the present invention provides a bone chisel that includes an elongated tubular structure having a first end and a bone-cutting end. The bone-cutting end is terminated in a transverse angle thereby creating an elliptical bone-cutting face.

In other aspects, the present invention provides an articular surface implant that includes an angled bearing element comprising a cylindrical member having a first end and a second end. The first end is formed at an angle that creates an elliptical face of the first end, and the first end defines a load-bearing surface of an articular surface.

In yet another aspect, the present invention provides an articular surface implant that includes an angled bearing element, a fixation element adapted to engage bone, and an intermediate mount element adapted to couple the angled bearing element to the fixation element.

In other aspects, the present invention provides an articular surface implant that includes an angled bearing element comprising a cylindrical member having a first end and a second end. The first end is formed at an angle that creates an elliptical face of the first end, and the first end defines a load-bearing surface of an articular surface. The cylindrical member also includes means formed thereon to engage bone.

It will be appreciated by those skilled in the art that although the following Detailed Description will proceed with reference being made to exemplary embodiments and methods of use, the present invention is not intended to be limited to these exemplary embodiments and methods of use. Rather, the present invention is of broad scope and is intended to be limited as only set forth in the accompanying claims.

Other features and advantages of the present invention will become apparent as the following Detailed Description proceeds, and upon reference to the Drawings, wherein like numerals depict like parts, and wherein:

DETAILED DESCRIPTION OF EXEMPLARY EMBODIMENTS

Figure 1:
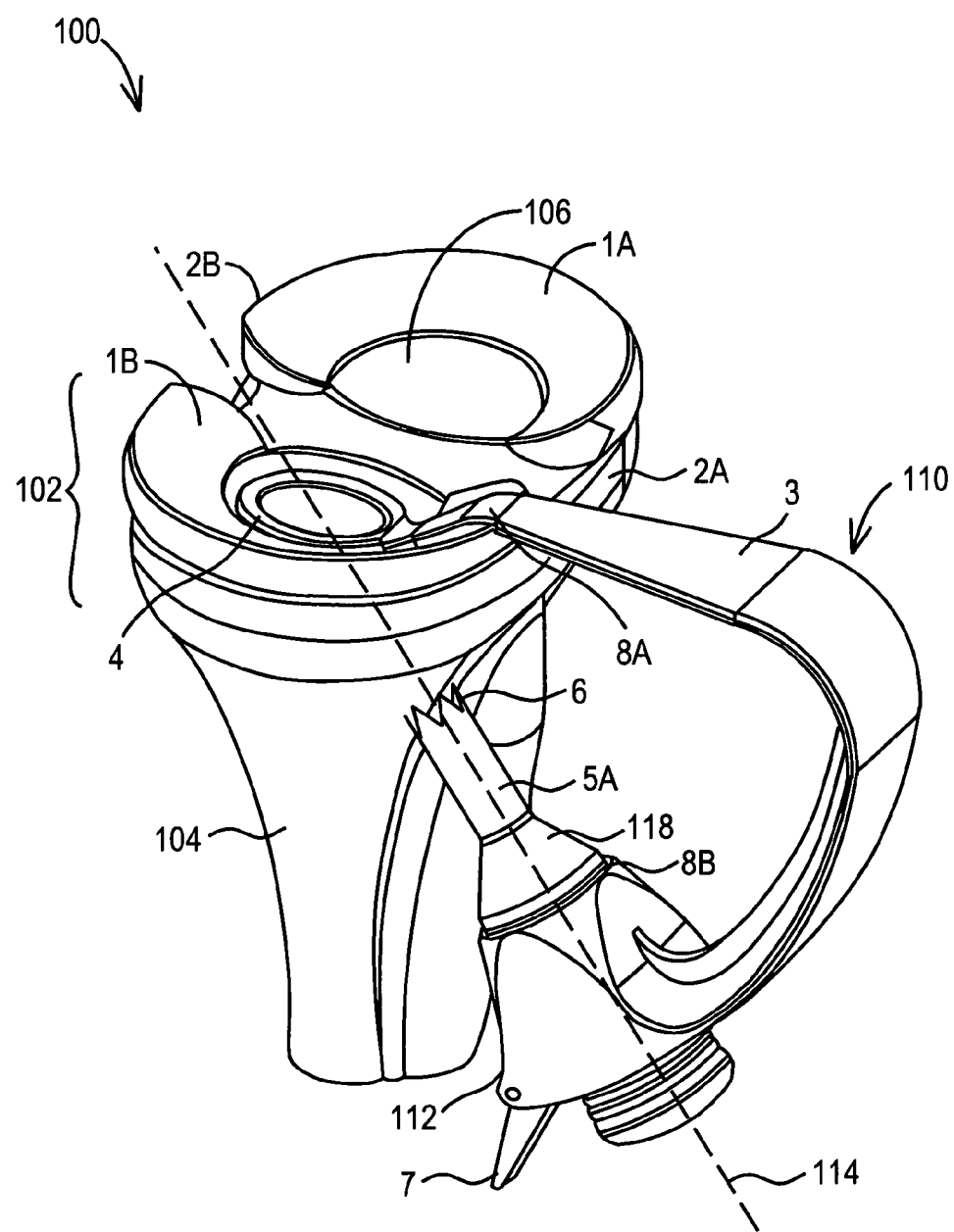
FIG. 1 is an in situ view of one exemplary drill guide according to the present invention.

FIG. 1 is an in situ view 100 of one exemplary drill guide according to the present invention. This figure depicts the proximal portion 102 of the tibia as well as the distal tibia 104. The knee contains a meniscus 1A and 1B in both the lateral and medial compartments, respectively. The meniscus is connected to the superior tibial surface by way of an anterior 2A and posterior 2B bony attachment. The meniscus is otherwise relatively mobile and glides along the top of the tibia 104 in concert with and as a partial constraint to the femoral condyle (not shown, but well understood in the art).

In one aspect of the present invention, a novel drill guide is provided. In one exemplary embodiment, a drill guide 110 is depicted in FIG. 1. The drill guide 110 of this exemplary embodiment generally includes a targeting ring 4, and angled boom 8A, a curved arm section 3 and a bore section 112. The targeting ring 4 may have a thickness that is narrow enough to be inserted between the femoral condyles and the superior tibial surface 106. The ring 4 may also be dimensioned to be approximately the same size and shape as the oval shaped implant that will eventually be delivered to the joint surface, as described more fully below. However, this is not a requirement of the present and only represents an exemplary shape of the ring.

The ring 4 is attached to the curved arm section 3 of the guide by an angled boom 8A that is configured to pass over the top of the meniscus 1B when the joint is accessed from one of two standard incisions used during arthroscopic surgery, the anterior-medial or anterior-lateral portal (these incisions are not depicted in FIG. 1, but are well understood in the art). The guide also contains a bore section 112 connected to the arm 3. In the exemplary embodiment, the bore section 112 is connected to the arm so that it creates an axis 114 that extends back through a center-point or near center-point within the central portion 116 of the oval targeting ring 4. The bore section 112 includes a hollow chuck 8B, a hollow collar taper 118 and a cylindrical bullet 5A. The bore section is sized to receive the cylindrical bullet. The cylindrical bullet 5A may be advanced within the chuck 8B until contact is made with bone surface of the tibia 104. To that end, the bullet 5A may include teeth 6 to enhance or secure contact with the bone surface of the tibia. A releasable ratchet 7 allows for advancement of the bullet 5A through the chuck 8B, and provides a locking mechanism to secure the bullet 5A into position to form a stable platform for subsequent steps.

Figure 3:
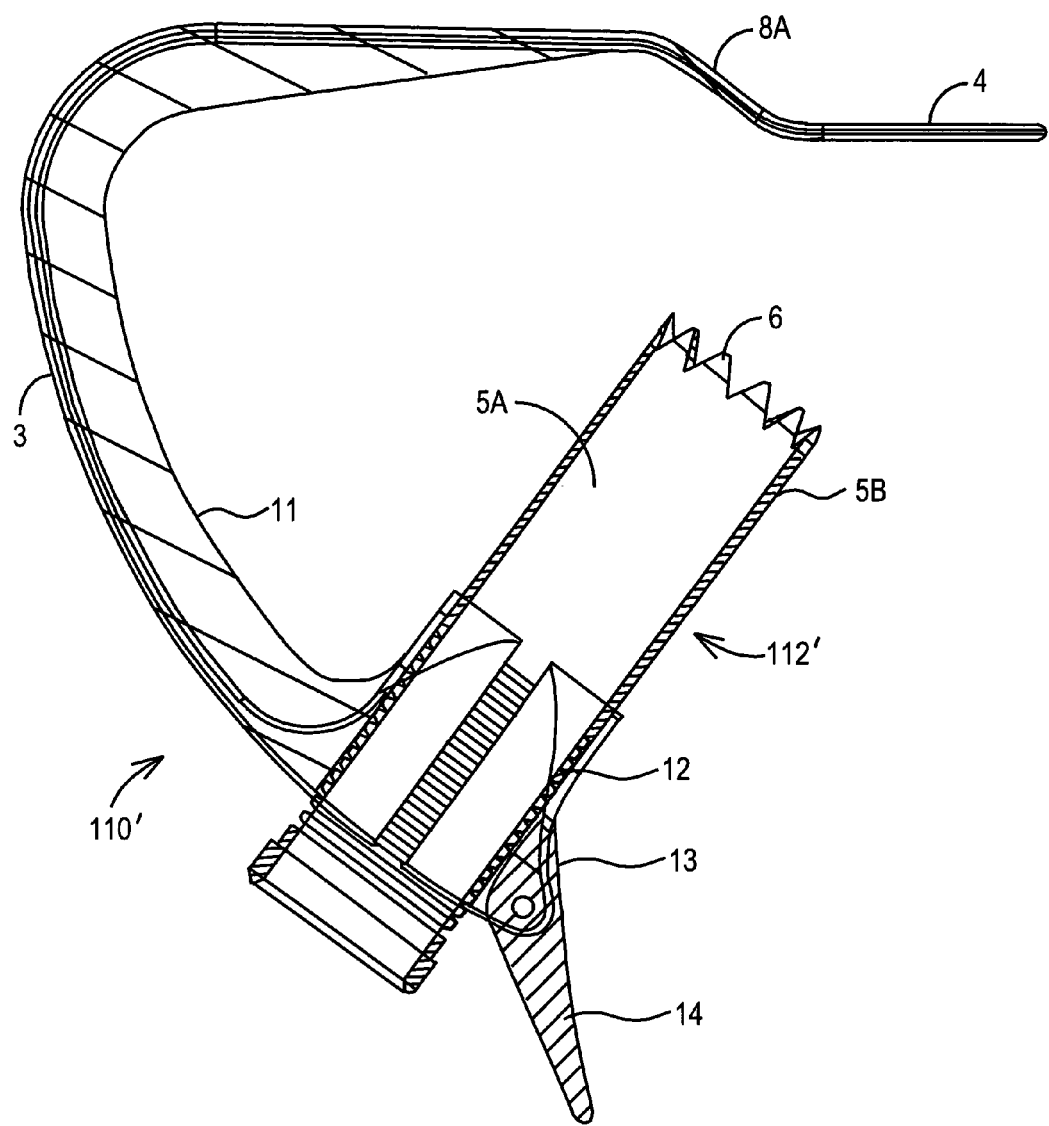
FIG. 3 is a side view of one exemplary drill guide according to the present invention.

FIG. 3 is a side view of another exemplary drill guide 110' according to the present invention. The arm section 3 may also include a stiffening central flange 11 in the arcuate portions of the arm 3. An alternative large bore bullet 5B may also be used in the guide. With either bullet (5A or 5B), the releasable ratchet mechanism may consist of a pawl 13 mounted pivotally on the chuck 8B. The bullet 5A or 5B may include a rack 12 generally defined as teeth on the side surface of the bullet. A portion of the pawl 14 may be loaded to pivotally actuate the pawl and disengage it from the rack.

Figure 2:
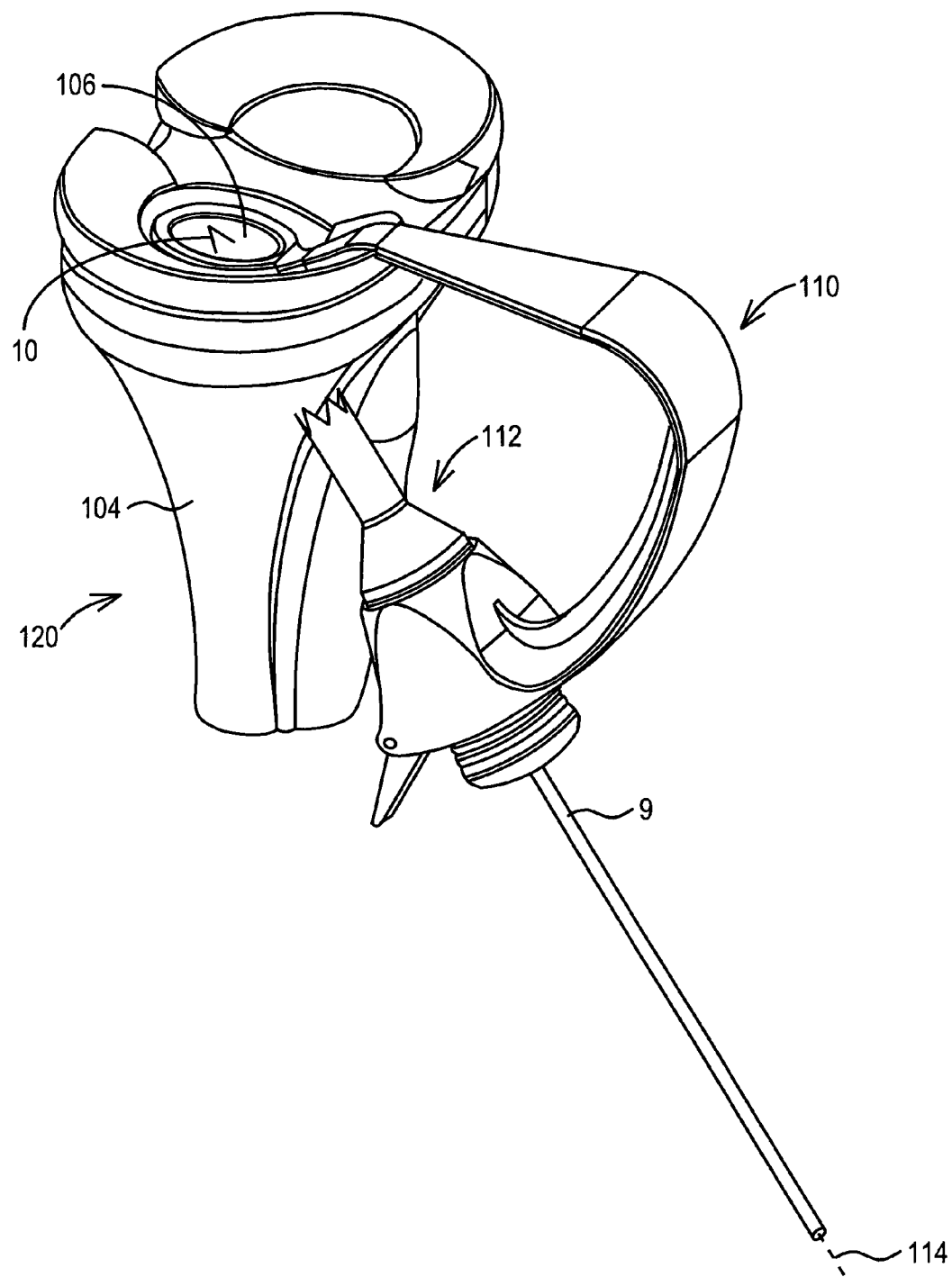
FIG. 2 is an in situ view of one exemplary drill guide and guide pin according to the present invention.

FIG. 2 is an in situ view 120 of one exemplary drill guide and guide pin according to the present invention. With the guide 110 in position, a guide pin 9 is inserted through the bore section 112 and drilled into the tibia 104. Preferably, the guide pin is drilled through the tibia along the axis 114 defined by the position of the bore section until the tip 10 of the drill 9 is visible in the center of the targeting ring 4.

Figure 4:
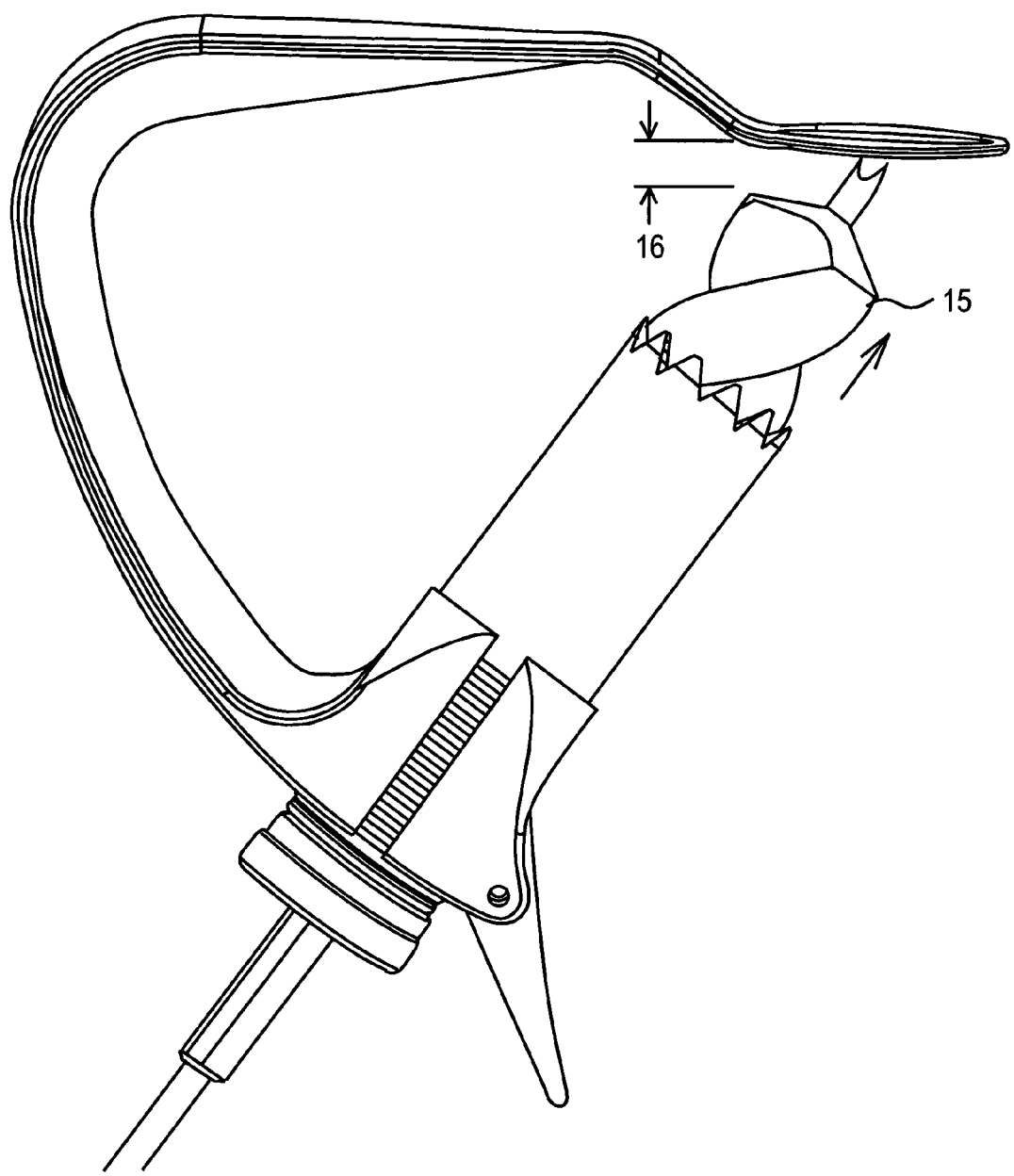
FIG. 4 is a side view of one exemplary drill guide and drill bit according to the present invention.

Referring now to FIG. 4, and once the guide pin 9 is properly positioned, a drill 15 is driven over the pin 9. In FIG. 4, the anatomical references are removed for clarity. The drill may have a diameter slightly larger than the diameter of implant (described below). In the exemplary embodiment, the drill is driven until it reaches a distance 16 that may be approximately 2–3 mm below the surface of the tibial articular surface 106. Techniques for determining this appropriate drilling distance based on a readable scale, or techniques including built in depth-stops in the guide or drill shaft are well described in the orthopedic art, and may be employed in the present invention. The drill utilized herein may be a conventional bone drill as is well understood in the art.

Figure 5:
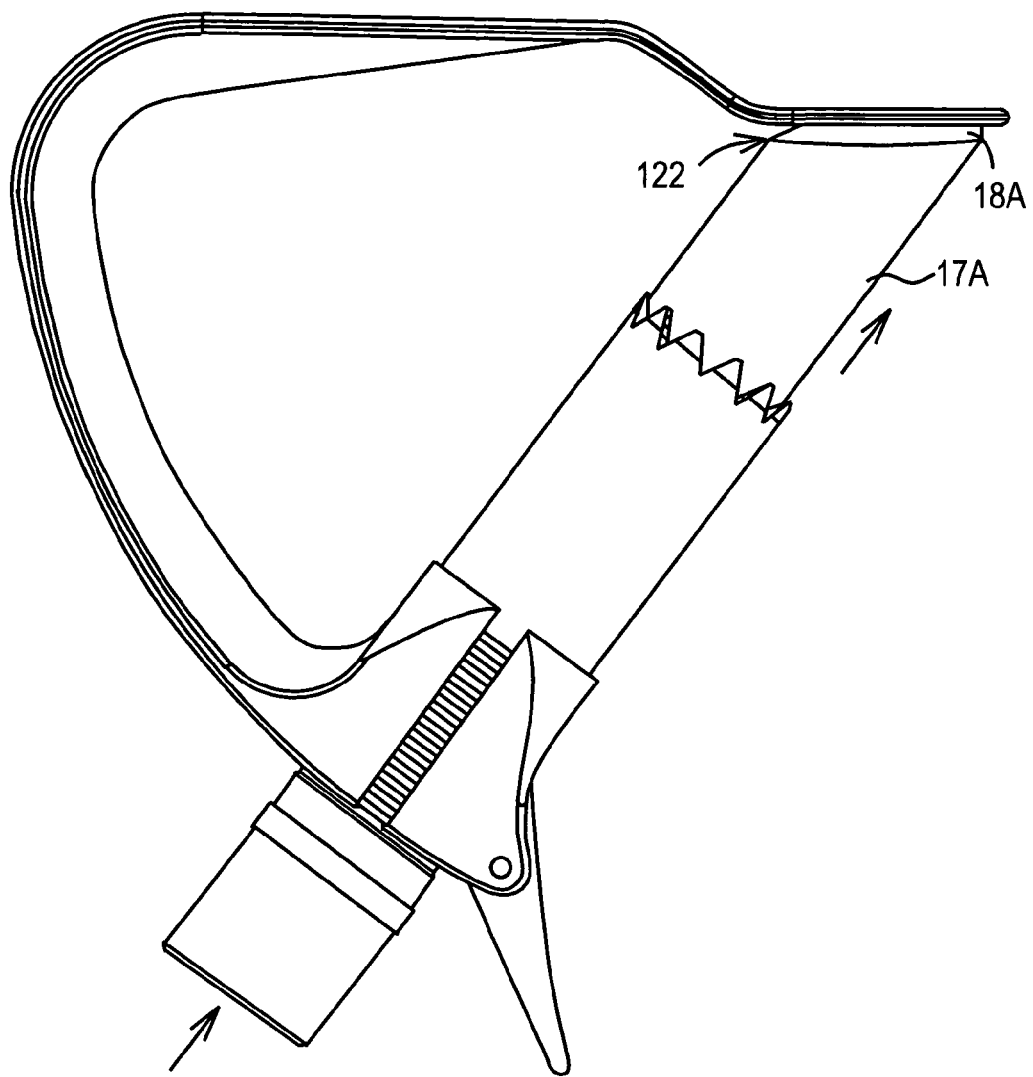
FIG. 5 is a side view of one exemplary drill guide and chisel according to the present invention.
Figure 6:
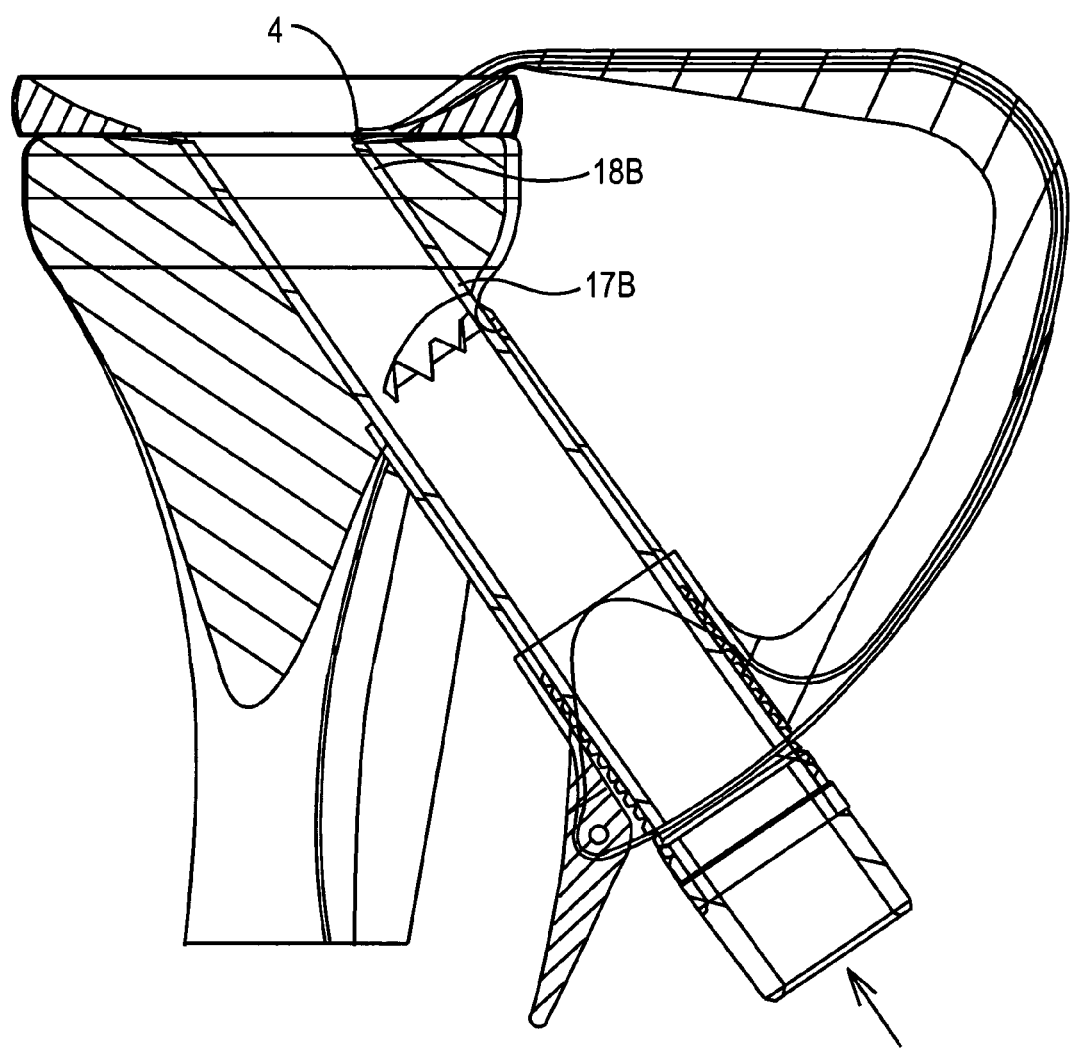
FIG. 6 is an in situ side view of one exemplary drill guide and chisel according to the present invention.

Next as depicted in FIG. 5, a cylindrical chisel 17A is introduced into the drilled tunnel and advanced up to the point were it contacts the end point of the previously drilled tunnel. This chisel of this exemplary embodiment includes a tip configuration comprising an angled transverse cut 122 across the chisel diameter. The chisel is essentially an elongated tubular structure, and the angled transverse cut 122 creates an elliptical end face 18A to the tube section. This elliptical geometry may correspond to the elliptical geometry of the tibial implant to be delivered, as well as the elliptical configuration of the targeting ring 4 of the drill guide. The chisel may include a beveled, sharp, tube tip, as depicted. Although not shown in the drawings, the chisel may include markings or keyed portions so that it will be driven in the proper rotational position relative to the oval targeting ring 19. To that end, the bore section 112 may include a key arrangement that is mated with the key on the chisel.

With the guide 110 held firmly in position, the chisel is impacted up to and against the underside surface of the targeting ring 4. To assist in the clean cutting of the bone and cartilage, the chisel and targeting ring may include some features (18B, to assist in the final alignment or cleaving of the compressed tissues.

Figure 7:
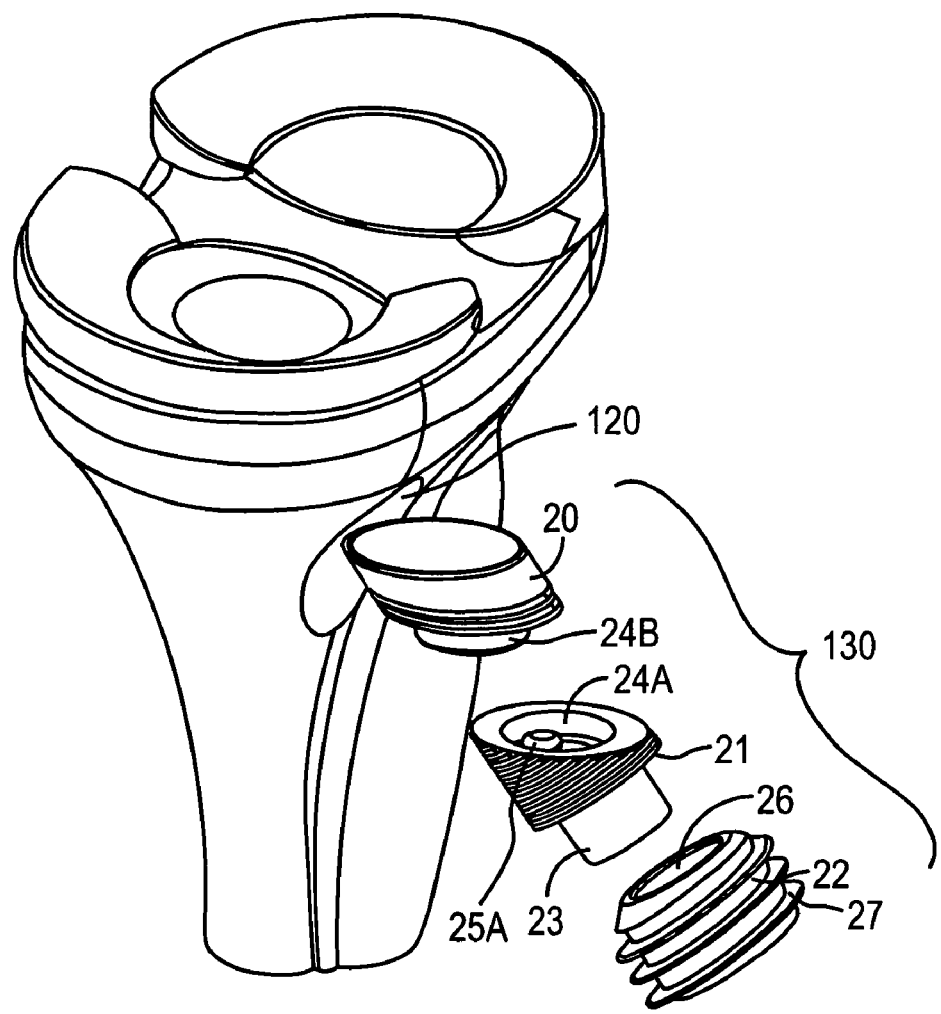
FIG. 7 is an exploded view of one exemplary implant according to the present invention.

The site is now prepared for implant delivery. FIG. 7 depicts an exploded view of one exemplary implant 130 according to the present invention. The implant 130 of the present invention is generally a cylindrical member that includes an angled bearing element comprising having a first end and a second end, where the first end is formed at an angle that creates an elliptical face of said first end. The first end defines a load-bearing surface of an articular surface. The implant may include three components, an angled bearing surface 20, an intermediate mount 21, and a fixation element 22. The bearing surface 20 may be fixed into the mount, for example, by a press-fit or snap-fit configuration between mating portions 24A, 24B of the underside of the bearing surface portion and the intermediate mount, respectively. An off-center boss 25A may be included in the mating portion 24A that fits into a matching off-center bore in the mating portion 24B of the bearing surface 20, to provide a rotational keying or alignment of the two components. Of course, the boss 25A may equally be provided in the mating portion 24B of the bearing surface 20. Those skilled in the art will recognize that numerous mechanical modifications may be made to the bearing surface 20 and/or intermediate mount 21 to provide rotational keying and/or alignment, and all such alternatives are deemed within the scope of the present invention. When the two components are assembled, a relatively continuous cylindrical shaft of the two components is formed.

Figure 8:
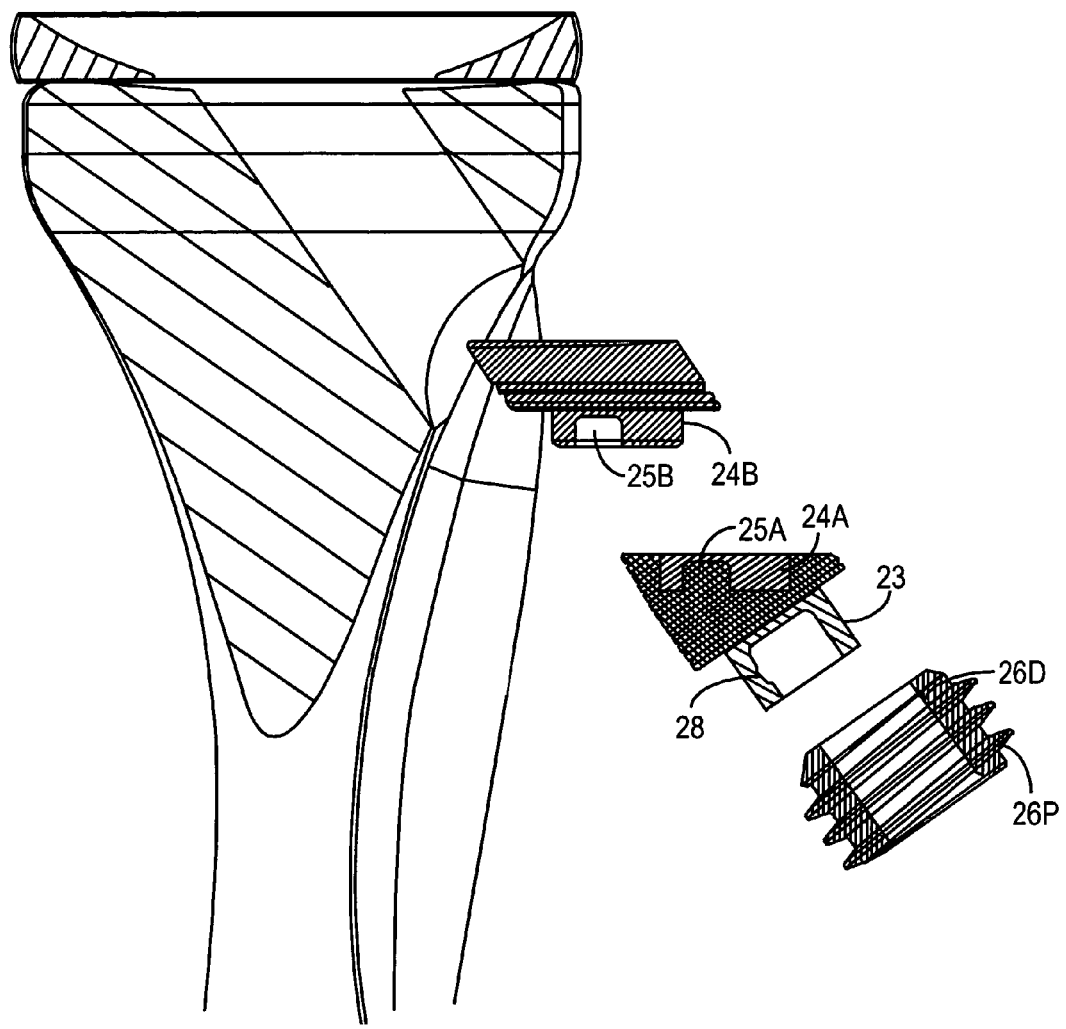
FIG. 8 is an exploded view of one exemplary implant according to the present invention.

FIG. 8 depicts an exploded cross-sectional view of the implant. The fixation element 22 of this exemplary embodiment is a screw with a modified cancellous thread form 27 and a root diameter that is approximately the same as the diameters of the bearing surface and the mount. In the exemplary embodiment, the root diameter is on the order of 10–20 mm. The screw has a large thru-hole 26 at the proximal end of the screw, and a taper bore 26D at the distal end of the screw which mates and interlocks to the male taper boss 23 on the proximal end of the mount component 21. When the two components 21,22 are forced together, the taper surfaces 26D and 23 will interlock forming a rigid connection between the two components. The proximal end of the screw also contains a hex bore 26P suited for engagement with a large orthopedic male hexdriver.

Figure 9:
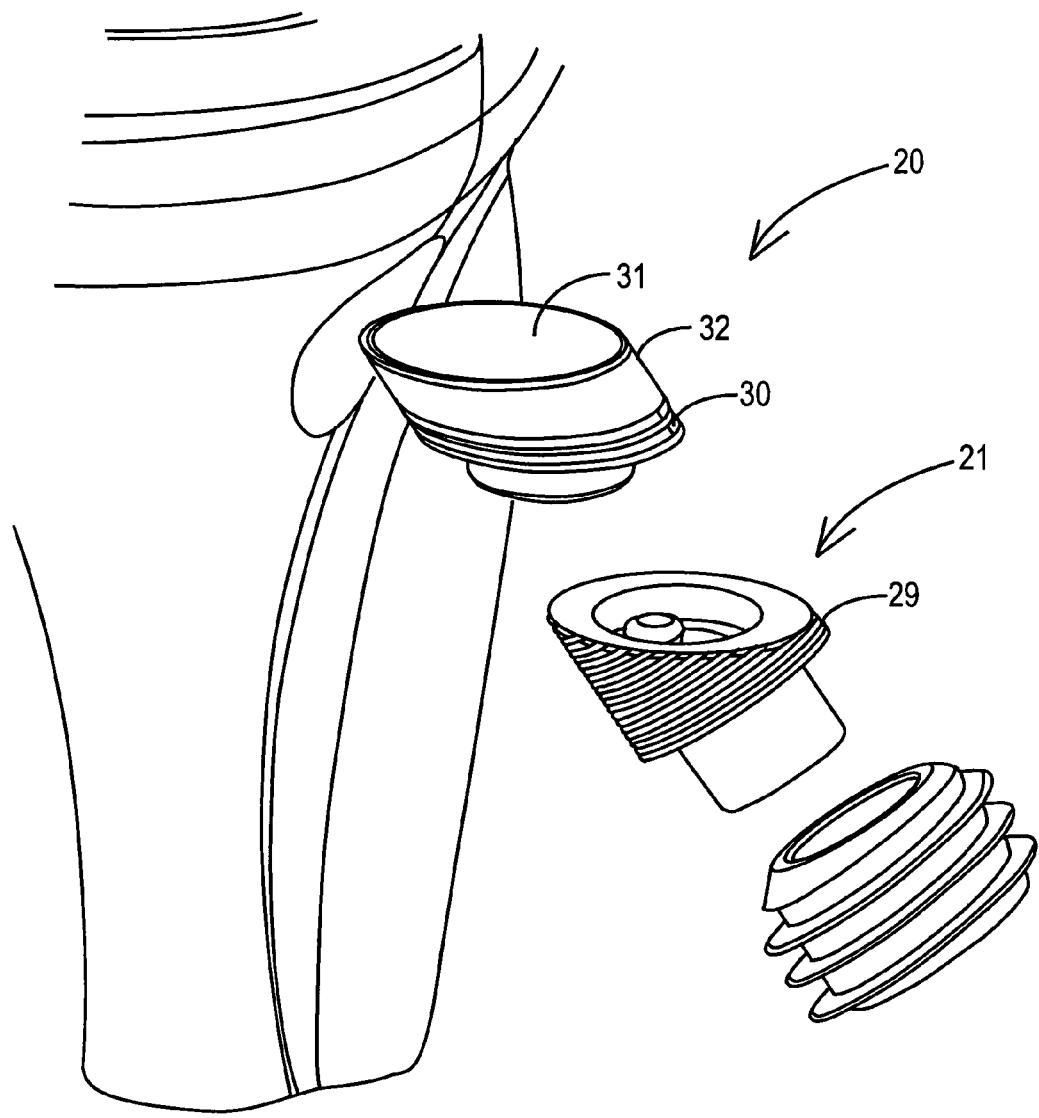
FIG. 9 is an exploded view of one exemplary implant according to the present invention.

FIG. 9 depicts another exploded view of the implant 130. The bearing surface component 20 may include grooves or rings 30 to aid in transferring mechanical loads to the surrounding bone, and may contain a contoured superior surface 31 to better match the existing articular surface. The intermediate mount 21 may also have similar load transferring features 29.

Figure 10:
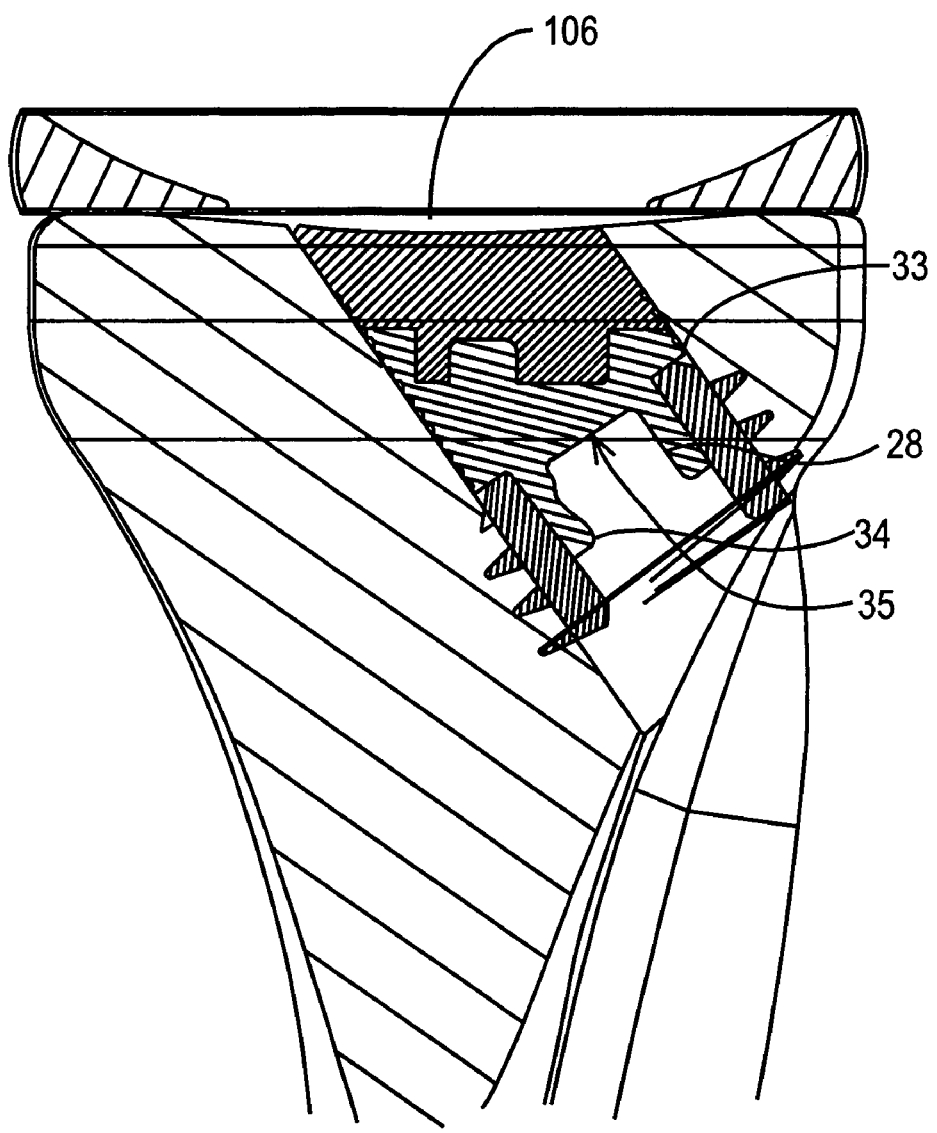
FIG. 10 is an in situ view of one exemplary implant according to the present invention.
Figure 11:
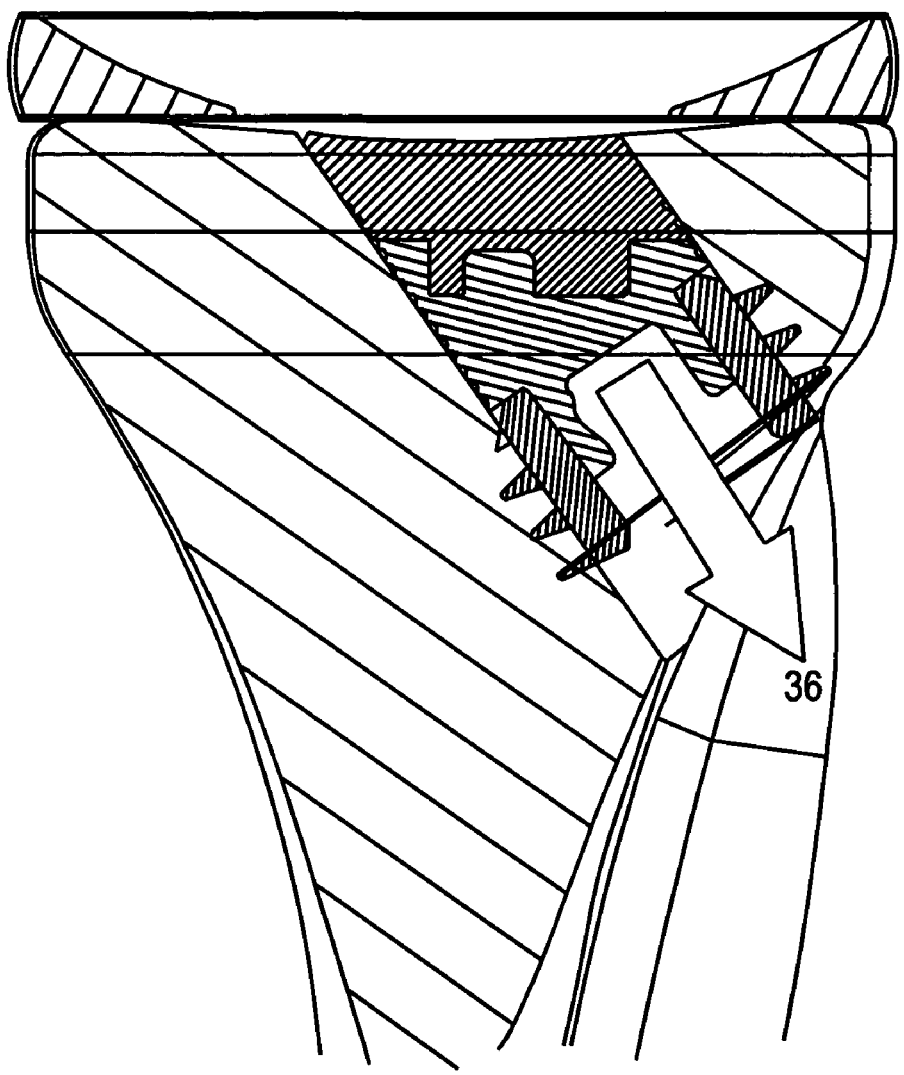
FIG. 11 is an in situ view of one exemplary implant according to the present invention.

FIG. 10 depicts the implant inserted into the bone. The proximal end of the mount component may include a bore 28 which allows for the insertion of a stand-off post 35 that works in conjunction with the hexdriver used for advancing the screw component. The stand-off permits the two components to remain slightly separated at the joint between the two devices 33 during the driving of the screw. This will allow for fine adjustment of the screw depth to bring the implant up to a position flush or slightly recessed to the existing articular surface 106 of the tibia. Using the stand-off post 35, engaged into the mount bore, the bearing surface and intermediate mount assembly can be rotated independently of the screw component to ensure it is properly aligned with respect to the tibial articular surface. Once all alignments are complete, a downward force 36 on the intermediate mount component will seat the tapers and lock all components into a fixed position, as depicted in FIG. 11.

Materials well known in the field of orthopedics can be used for the implant components. For example, UHMWPE for the bearing surface, and Titanium or Cobalt-Chromium Alloys used for the intermediate mount and fixation elements. However, as the most common cause for failure of such components is related to the wear debris of the UHMWPE, the bearing surface component may be formed out of alternate materials which might provide clinical advantages based on their hydrophilic, low-friction characteristics. For example, recent developments in the fields of durable polyurethanes and structural hydrogels suggest that these materials, loaded into a suitable base, could be effective alternatives when rigidly fixed in bone.

Figure 12:
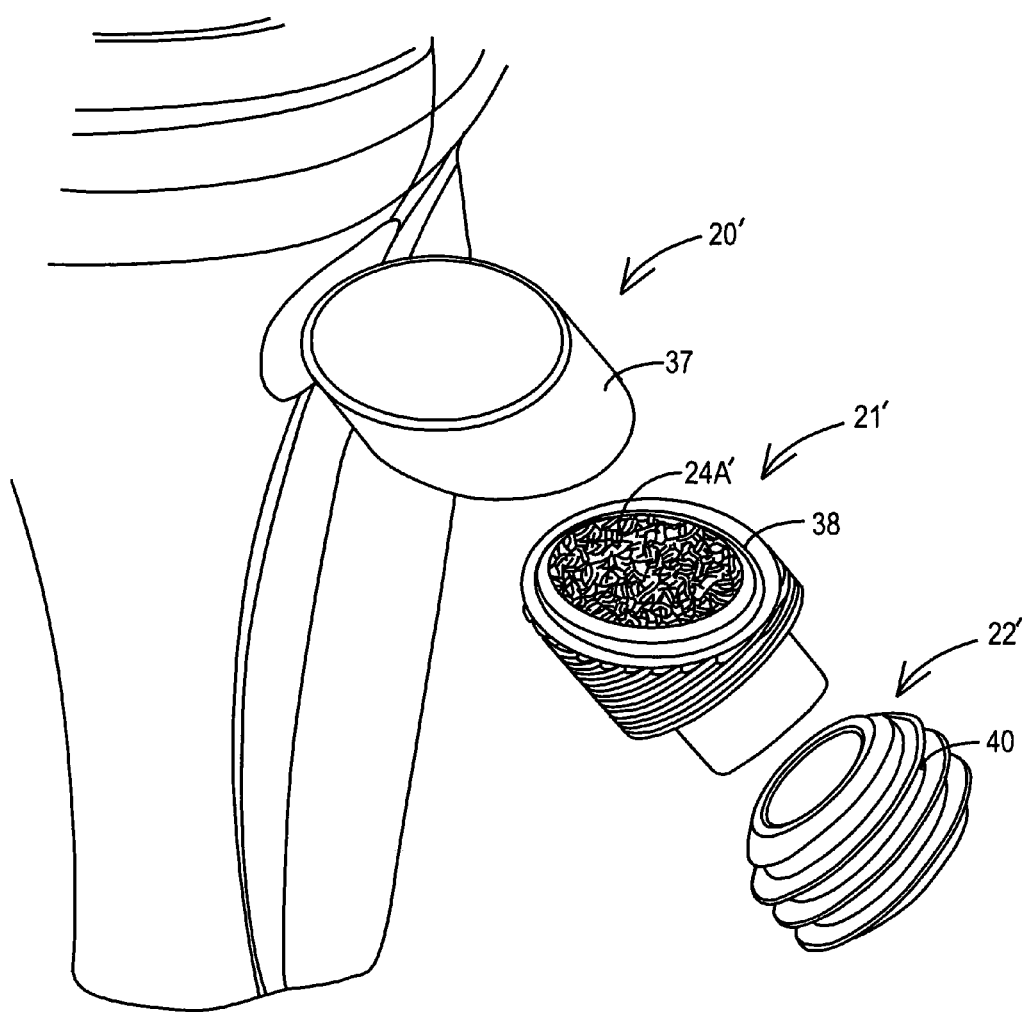
FIG. 12 is an exploded view of another exemplary implant according to the present invention.
Figure 13:
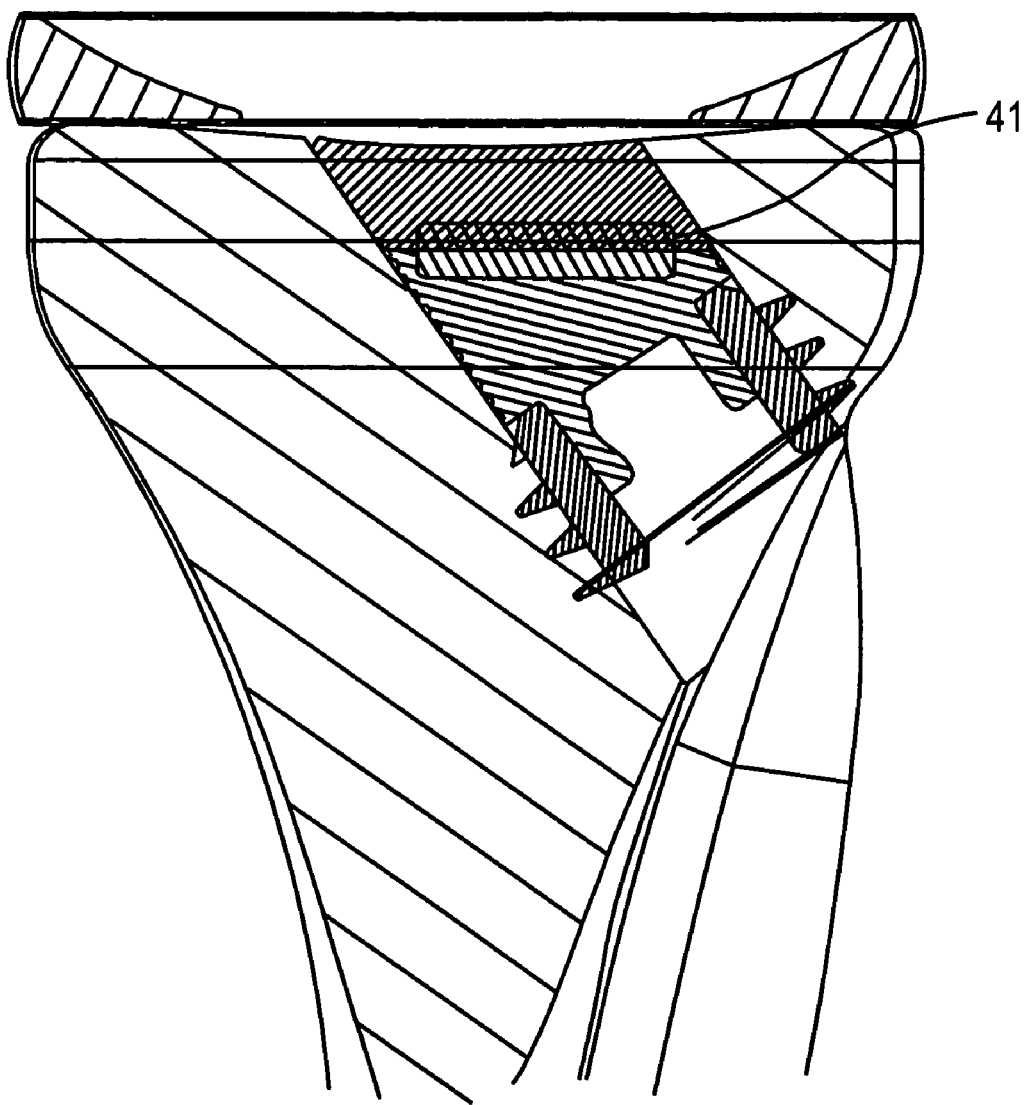
FIG. 13 is an in situ view of another exemplary implant according to the present invention.

FIG. 12 depicts an alternative exemplary embodiment of the implant of the present invention. In this embodiment, the intermediate mount 21' may include a wound and compressed wire portion 38 that may sintered into the bore 24A' in the intermediate mount. The wire portion 38 may be formed of a material similar to the material used for the intermediate mount. This may be advantageous if the wire portion and mount are heated to a temperature approaching the melting temperature for the materials, the components can fuse together to form a solid mass with controllable pore sizing to include a semi-continuous network of open spaces (i.e., porous material). The porous material may then be utilized as a base and a gel or elostomeric material may be cast into it. As shown in FIG. 13, this provides a mechanical interlock 41 between the cast material and the structural base.

Numerous alternatives will be recognized by those skilled in the art. For example, the angled bearing element can include fixation means attached thereon, so that the bearing element is screwed directly into bone. Alternatively, the fixation system could include an angled bearing element and a fixation element, without the need for an intermediate mount member. These and other alternatives will become apparent from the foregoing detailed description, and all such alternatives are deemed within the scope of the present invention, only as limited by the claims.

The invention claimed is:

1. An articular surface implant, comprising an angled bearing element comprising a cylindrical member having a first end and a second end, said first end being formed at an angle that creates an elliptical face of said first end, said first end defining a load-bearing surface of an articular surface, a fixation element adapted to engage bone, and an intermediate mount element adapted to couple said angled bearing element to said fixation element, said intermediate mount element being adapted to engage a driving tool to rotate said intermediate mount independent of said fixation element.

2. An implant as claimed in claim 1, wherein said elliptical face is formed of a durable polyurethane.

3. An implant as claimed in claim 1, wherein said elliptical face is formed of a hydrogel.

4. An implant as claimed in claim 1, wherein said elliptical face is formed of a UHMWPE material.

5. An articular surface implant, comprising an angled bearing element comprising a cylindrical member having a first end formed at an angle that creates an elliptical face defining a load-bearing surface of an articular surface, and a second end comprising a post extending from a face of said second end, a fixation element comprising threads adapted to engage bone, and an intermediate mount element adapted to couple said angled bearing element to said fixation element, said post being adapted to engage said intermediate mount.

6. An articular surface implant as claimed in claim 5, wherein said second end is formed at an angle that creates an elliptical face of said second end, said post extending from the face of said second end.

7. An articular surface implant as claimed in claim 5, said angled bearing element further comprising at least one of grooves or rings extending along at least a portion of the outer periphery thereof, said grooves or rings adapted to engage bone.

8. An articular surface implant as claimed in claim 5, wherein said angled bearing element and said intermediate mount element are adapted to couple together, and wherein said intermediate mount is adapted to engage a driving tool to rotate said intermediate mount and said angled bearing element independent of said fixation element.

9. An articular surface implant as claimed in claim 5, wherein said intermediate mount element comprises a base comprising wire thereby forming a porous base, said angled bearing element formed in said base.

10. An articular surface implant as claimed in claim 9, wherein said angled bearing element is formed of a polyurethane and/or hydrogel material.

11. An articular surface implant comprising an angled bearing element comprising a cylindrical member having a first end formed at an angle that creates an elliptical face defining a load bearing surface of an articular surface, a fixation element comprising threads adapted to engage bone, and an intermediate mount element adapted to couple said angled bearing element to said fixation element, wherein said intermediate mount element comprises a first end and a second end, said first end having a key portion formed therein adapted to engage said angled bearing element.

12. An articular surface implant as claimed in claim 11, wherein said first end is formed at an angle that creates an elliptical face of said first end, said second end comprising a post extending from the face of said second end, said post adapted to engage said fixation element.

13. An articular surface implant as claimed in claim 12, wherein said post is adapted to engage a driving tool to rotate said intermediate mount independent of said fixation element.

* * * * *